United States Patent
Watanabe et al.

[11] Patent Number: 5,259,843
[45] Date of Patent: Nov. 9, 1993

[54] MEDICAL CONNECTOR FOR ATTACHING TO LIQUID INTRODUCING TUBE

[75] Inventors: Hiroaki Watanabe; Yuji Ogawa, both of Ohita, Japan

[73] Assignee: Kawasumi Laboratories Inc., Tokyo, Japan

[21] Appl. No.: 791,983

[22] Filed: Nov. 14, 1991

[51] Int. Cl.⁵ ............................................. A61M 5/14
[52] U.S. Cl. .................... 604/256; 604/283; 604/905; 604/408; 128/912; 285/4; 285/901
[58] Field of Search .......... 604/408, 905, 283, 282, 604/284, 256; 128/912; 285/2, 3, 4, 901

[56] References Cited

U.S. PATENT DOCUMENTS

| | | | |
|---|---|---|---|
| 3,058,472 | 10/1962 | Thornton | 604/256 |
| 3,127,892 | 4/1964 | Bellamy et al. | 285/4 X |
| 3,217,710 | 11/1965 | Beall et al. | 604/408 |
| 3,342,179 | 9/1967 | Ellmann | 604/408 |
| 3,513,849 | 5/1970 | Vaillancourt et al. | 604/256 |
| 3,633,586 | 1/1972 | Sheridan | 285/901 X |
| 3,741,217 | 6/1973 | Cierico | 604/256 |
| 3,846,030 | 11/1974 | Katt | 403/2 |
| 3,916,929 | 11/1975 | Brown | 137/68 |
| 4,493,348 | 1/1985 | Lemmons | 141/1 |
| 4,508,367 | 4/1985 | Oreopoulos et al. | 285/3 |
| 4,927,423 | 5/1990 | Malmborg | 604/88 |
| 4,963,132 | 10/1990 | Gibson | 604/256 |
| 5,057,093 | 10/1991 | Clegg et al. | 604/283 |

Primary Examiner—John D. Yasko
Assistant Examiner—Mark O. Polutta
Attorney, Agent, or Firm—Michael J. Striker

[57] ABSTRACT

A medical connector to be attached to a liquid introducing tube has a first connecting part adapted to be connected to one portion of a medical liquid introducing tube, a second connecting part adapted to be connected to another portion of the medical liquid introducing tube and being formed integrally with the first connecting part, a breaking portion formed between the first and second connecting parts and adapted to be broken under finger pressure, and a seal cap for sealing an opening of the second connector part after breaking the breaking portion.

7 Claims, 7 Drawing Sheets

MEDICAL CONNECTOR FOR ATTACHING TO LIQUID INTRODUCING TUBE

BACKGROUND OF THE INVENTION

The present invention relates to a medical instrument provided with a main bag body and a liquid introduction tube to be connected to said bag body, and more particularly to a connector which is attached on a half way of the liquid introduction tube for dividing said tube.

Figure 16:
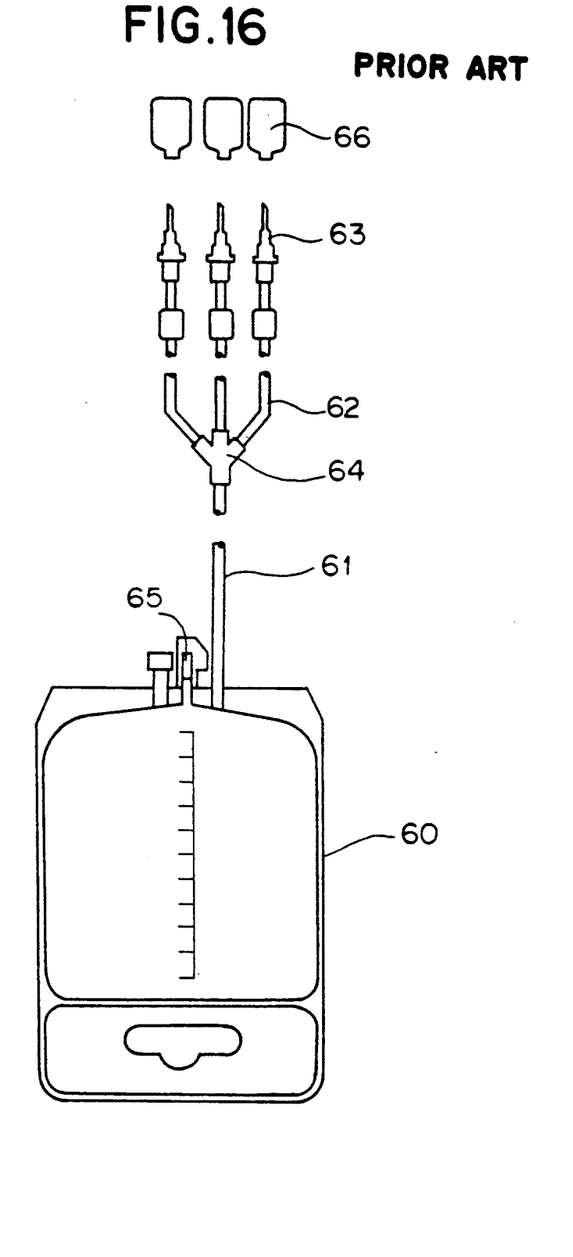
FIG. 16 is a view showing one example of existing bags of the high calorie medical liquid.

For example, a patient after having had a surgical operation is injected with a medical liquid of high calorie which has been prepared from various medical liquids. FIG. 16 shows one example of existing high calorie medical liquid bags. A flexible bag body is connected, at an upper end, to a bendable main liquid introduction tube 61 and a liquid sending mouth 65. The main tube 61 is connected, via a branching tube 64, to a plurality of branched tubes 62. Each of the branched tube 62 has a medical liquid introduction needle 63.

When the liquid bag 63 is used, the needle 63 is pierced into a required bottle 66 holding the medical liquid to introduce the medical liquid of a predetermined amount into the main bag body 60 through the branched tube 62 and the main tube 61, so that a desired medical liquid is prepared.

When the preparation of the medical liquids is accomplished, the main tube 61 is blocked at a half way thereof, and after the upstream portion of the blocked part is cut off by scissors, the liquid sending mouth 65 is connected with a known liquid sending set, and the medical liquid in the bag 60 is injected into the patient.

As a way of blocking the above mentioned main tube 61, for example, the branched tube 62 is tightly knotted, molten, or closed with a stop clamp.

However, such stopping or sealing operations of the main tube 61 are troublesome, and if the sealing by knotting, melting or clamping is incomplete, the liquid in the bag 60 runs out from the cut portion of the tube 61, or an outer air is absorbed thereinto and pollutes the medical liquid.

SUMMARY OF THE INVENTION

It is an object of the present invention to provide a connector which easily divides the liquid introduction tube to be connected to a medical liquid bag at a desired portion, and air-seal as the divided portion. It is also an object of the present invention to provide a medical liquid introduction instrument using said connector.

DESCRIPTION OF THE PREFERRED EMBODIMENTS

Figure 1:
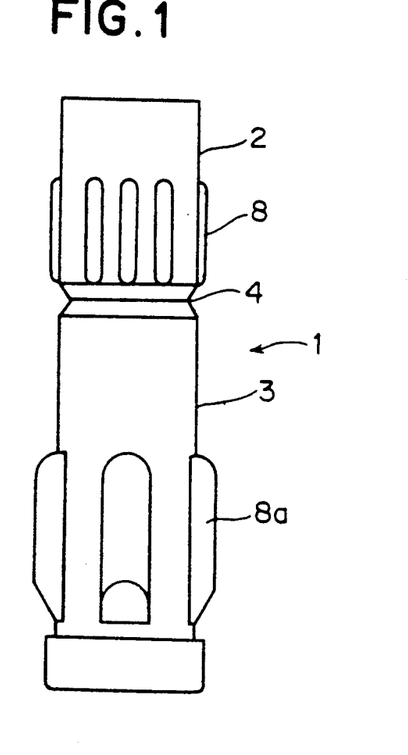
FIG. 1 is a front view of the connector of this invention.

A connector 1 shown in FIG. 1 has a first connecting part 2 and a second connecting part 3 which are integrally formed in a cylindrical shape with a hard synthetic resin. In a boundary of the both parts, a breaking portion 4 is defined by a groove extending in a circumferential direction. The breaking portion has a thickness such that it may be broken when the connector 1 is twisted with the fingers (pushed and bent).

Figure 2:
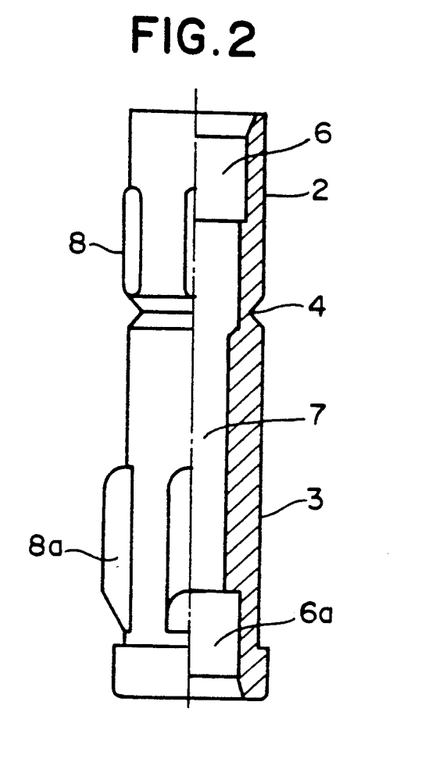
FIG. 2 is a half cross-sectional view of the connector of FIG. 1.

The first connecting part 2 is circumferentially formed with plural projecting slip stoppers 8 on an outer periphery. It has, as seen in FIG. 2, a large diameter opening 6 at a front end in an interior thereof, into which a later mentioned bendable tube 14 is inserted.

The second connecting part 3 is longer than the first connecting part 3 in an axial direction and is circumferentially formed with plural projecting slip stoppers 8a on an outer periphery. It also has a large diameter opening 6a at a rear end in an interior thereof into which a later mentioned bendable tube 15 is inserted. A liquid flow path 7 passe through the interior of the first connecting part 2 and the second connecting part 3.

The connector 1 can be broken at the breaking portion 4 by grasping the first and second connecting parts 2 and 3 with the fingers and twisting each other in opposite circum-ferential directions. The slip connectors 8, 8a are served therefor.

Figure 3:
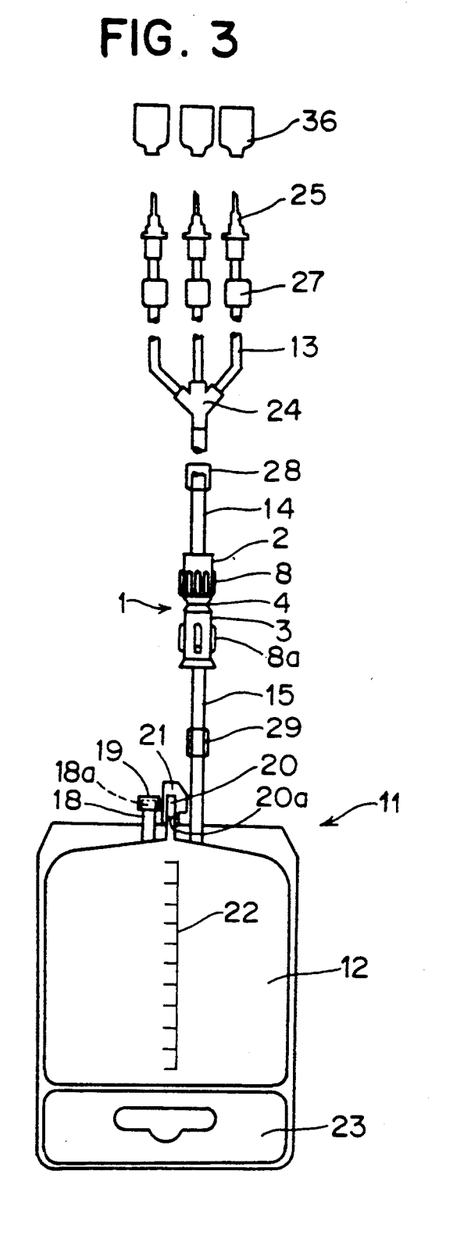
FIG. 3 is a view of the medical instrument of this invention.

FIG. 3 shows a high calorie liquid bag set 11 provided with the above mentioned connector 1. The bag body 12 is composed of two superposed sheets of the flexible synthetic resin such as an ethylene-acetic vinyl or a polyvinylchloride which are molten and combined on the circumferences thereof. The bag 65 is provided with a volumetric scale 22 on the outer surface, and formed with a hanger 23 for suspending the bag body 12 from a hook of a suspender.

The bag 12 has on its top a mixing tube 18, a transferring tube 20 and an introduction tube 15 of the second medical liquid. The mixing tube 17 has on its head a cap 19 provided with a rubber stopper 18a therewithin. It is used for mixing a new medical liquid into the bag 12 through an injection needle pierced in the rubber stopper 18a. The transferring tube 20 is pierced with a needle of a liquid transferring set (not shown) for injecting the medical liquid into the patient's blood vessel via said set. The transferring tube 20 is, at non-using, closed with a closing plate 20a in a flowing path, and is air-protected with a protector 21 on the outside. When using, the protector 21 is broken to expose a mouth, and the needle of the liquid transferring set is inserted into the tube 20 to break the closing plate 20a.

With respect to the connector 1, the second medical liquid introducing tube 15 is inserted at its front end into the large diameter opening 6a of the second connecting part 3 (FIG. 2), and is secured with an adhesive. The first medical liquid introducing tube 14 is inserted at its rear end into the large diameter opening 6a of the first connecting part 2, and is similarly secured with the adhesive. The tube 14 is connected at its front end with a branching tube 24 having three connecting mouths which continue to branched medical liquid introducing tubes 13 having liquid introducing needle 25 at the front end portion.

The respective tubes 14, 15 and 13 are composed of bendable synthetic resin such as polyvinylchloride, and the branched tubes 13 are attached with known clamps 27, 28, 29.

The high calorie liquid bag 11 shown in FIG. 3 is used in the following manner: Medicine bottles 36 are charged with different kinds of medical liquids respectively. One of the liquid introducing needles 25 is pierced into the mouth of a required bottle 36. The clamps 28, 29 are then opened, and the clamp 27 is closed. The clamp 27 is released to introduce the medical liquid with the aimed bottle 36 into the bag 12 in a required amount through the branched tube 13, the first liquid introduction tube 14, the connector 1 and the second liquid introduction tube 15. Subsequently, the clamp 27 is closed, and another needle 25 is inserted into another bottle 36 so as to introduce the medical liquid into the bag 12 in the same manner as said above.

Figure 4:
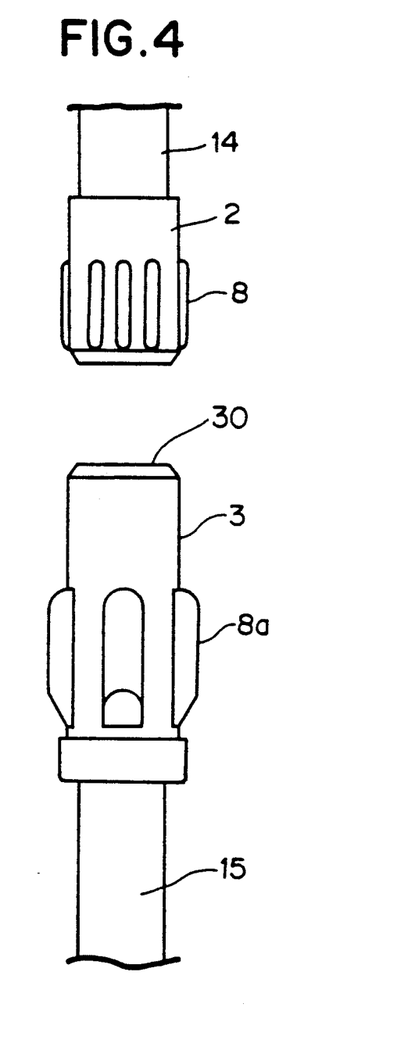
FIG. 4 is a front view showing that the connector of the invention is broken at a breaking portion thereof.
Figure 5:
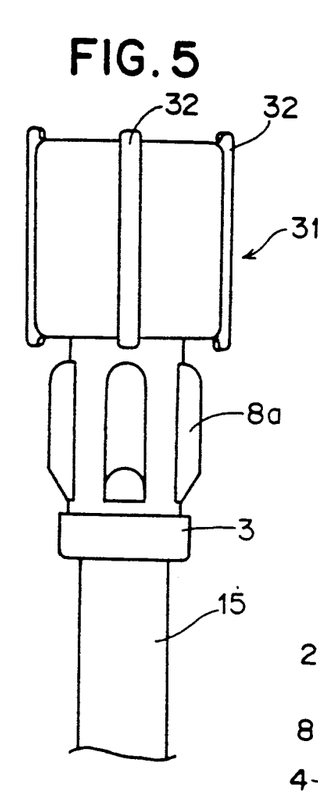
FIG. 5 is a front view showing that a seal cap is mounted onto a second connecting part of this invention.

Thus, the different kinds of the medical liquids are poured into the bag 12. After a medical liquid to be sent has been prepared, the clamps 28, 29 are closed to avoid air and unnecessary liquids from going into the bag 12. The first connecting part 2 and the second connecting part 3 of the connector 1 are twisted with the fingers in opposition to each other so as to break the breaking portion 4 and separate the both parts 2 and 3 as shown in FIG. 4. The opened portion 30 of the second connecting part 3 is crowned with a seal cap 31 as seen in FIG. 5 to provide a liquid sealing in the opened portion 30. The seal cap 31 has plural projecting slip stoppers 32 on the outer circumference. When the seal cap 31 is crowned on the opened part 30, the projections 32 and slip stoppers 8a of the second connecting part 3 are twisted opposite to each other, whereby the seal cap 31 is forcibly mounted onto the opened portion 30.

After the first connecting part 2 and the second connecting part 3 of the connector 1 have been divided, the hanger 23 of the bag 12 is suspended from the hook of the suspender. The protector 21 covering the liquid transferring tube 20 is broken, so that the needle of the known liquid transferring set (not shown) passes through the tube 20, and pierces into the patient's blood vessel for sending the medical liquid to him.

Figure 6:
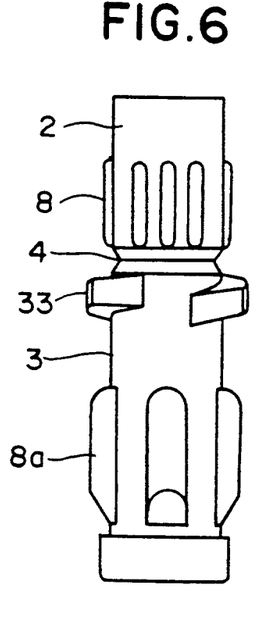
FIG. 6 is a plan view showing another embodiment of a connector of the invention.
Figure 7:
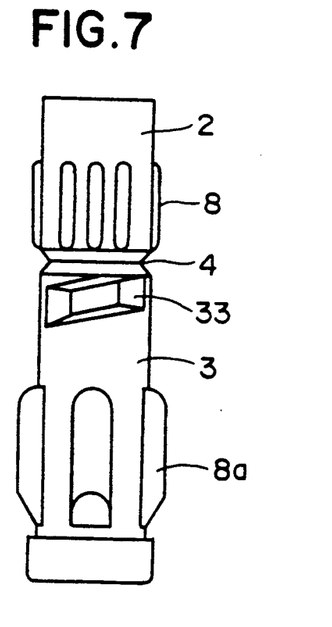
FIG. 7 is a side view of the connector of FIG. 6.
Figure 8:
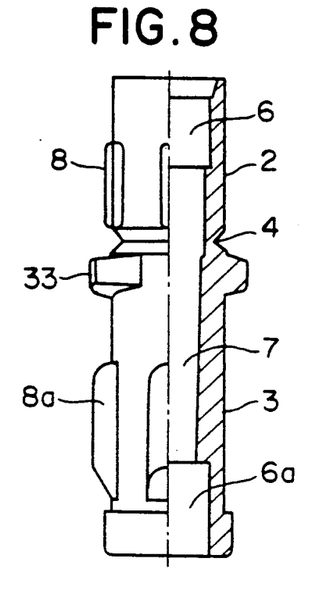
FIG. 8 is a half cross-sectional view of the connector of FIG. 6.
Figure 9:
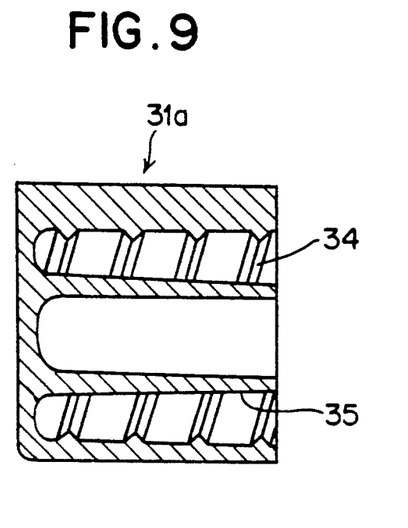
FIG. 9 is a cross-sectional view of a seal cap to be crowned onto the connector of FIG. 6.

FIGS. 6, 7 and 8 illustrate another embodiment of this invention. Herein, thread ridges 33 are formed on both sides of the outer circumference at the upper end of the second connecting part 3. FIG. 9 is the cross-sectional view of a seal cap 31a to be mounted on the opening of the second connecting part 3. At the center of the interior of the seal cap 31a, an inner cylindrical part 35 is provided for inserting into the opening (a liquid path 7) of the second connecting part 3, and is tapered in the outer shape along the length. The seal cap 31a is defined in the interior with a female screw 34 for the thread ridge 33 of the second connecting part 3.

The seal cap 31a is mounted on the opening (the liquid path 7) of the second connecting part 3 after having separated the first connecting part 2 and the second connecting part 3 at the breaking part 4. When the seal cap 31a is rotated, the female screw 34 is screwed with the thread ridges 33 of the second connecting part 3, and the inner cylindrical part 35 is urged into the liquid path 7. Thereby, the seal cap 31a is forcibly mounted on the opening of the second connecting part 3, and this opening is water-sealed and air-sealed by means of the inner cylindrical part 35.

Figure 10:
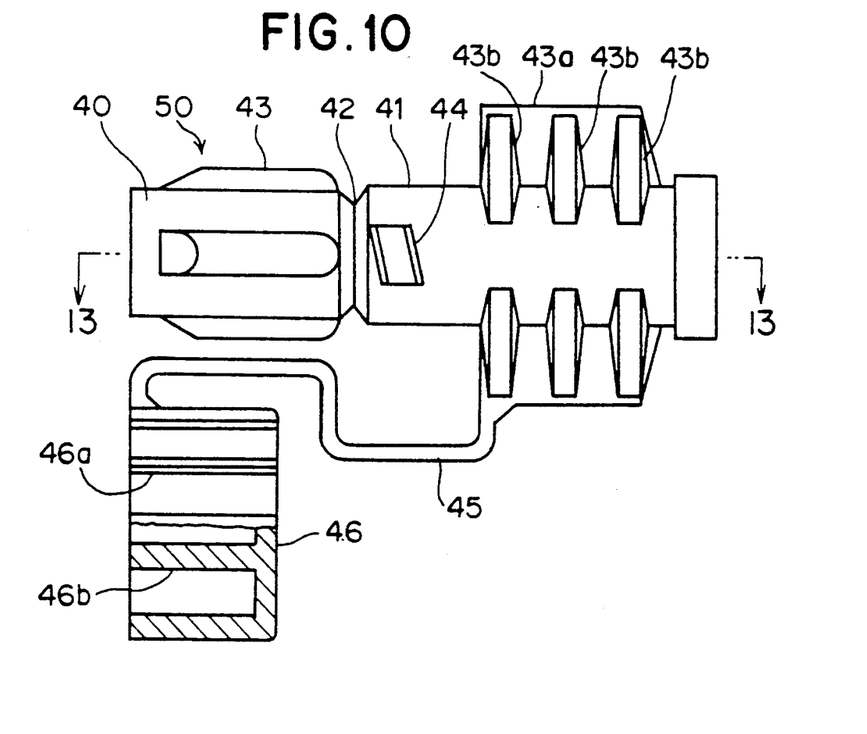
FIG. 10 is a front view, partially in section, of a further connector of this invention.
Figure 11:
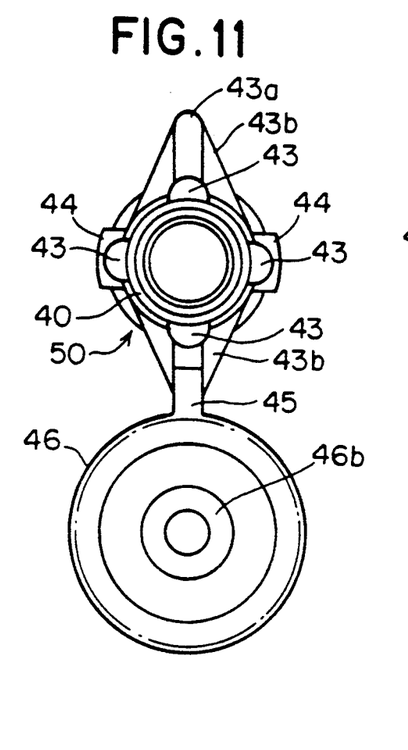
FIG. 11 is a left side view of the connector of FIG. 10.
Figure 12:
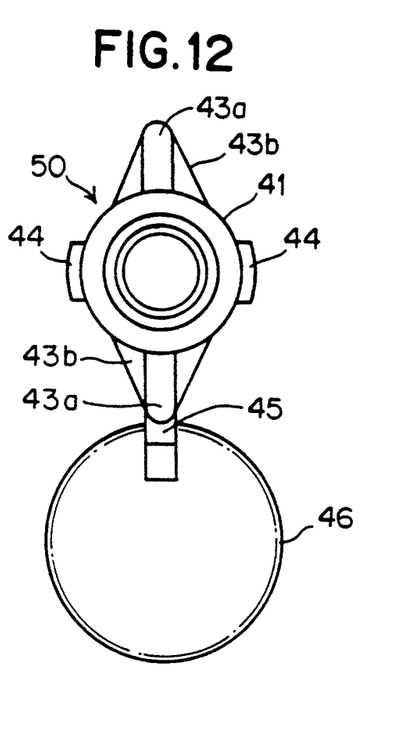
FIG. 12 is a right side view of the connector of FIG. 10.

FIGS. 10 through 14 show a further embodiment of the invention. A connector 50 has, as seen in FIG. 10, a first connecting part 40 and a second connecting part 41, which are integrally formed in cylindrical shapes of hard synthetic resin. A breaking portion 42 is provided at the boundary between said parts 40 and 41, which is broken by twisting the connector 50. The members are formed as in the embodiment of FIG. 1.

Figure 13:
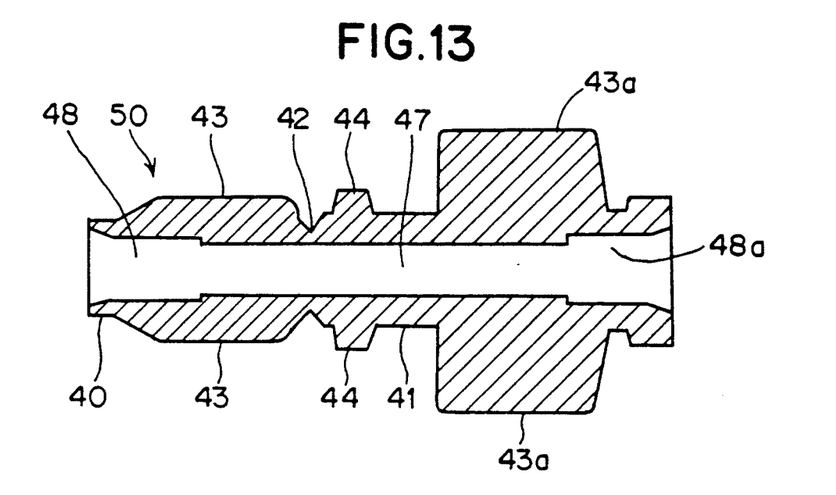
FIG. 13 is a cross-sectional view of the connector along A—A line thereof.

The first connecting part 40 has plural projecting slip stoppers 43 on the outer circumference, and is formed with a large diameter opening 48 at the front end of the interior as shown in FIG. 13 into which said first medical liquid introducing tube 14 is inserted.

The second connecting part 41 has slip stoppers 43a projecting in upper and lower directions at the outer part of the rear end, and a plurality of supporting ribs 43b located at predetermined spaces.

Figures 14, 15:
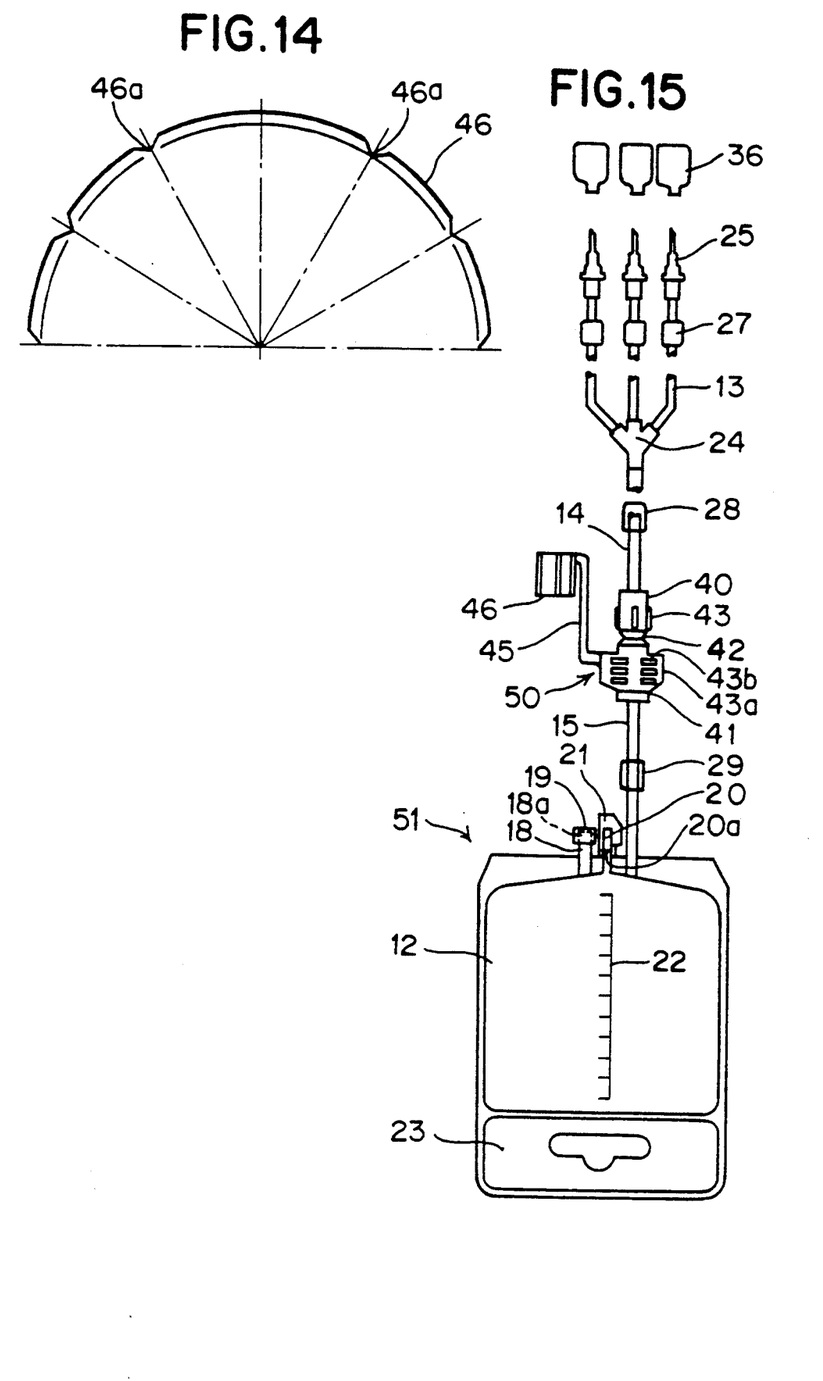
FIG. 14 is a partially enlarged view of a seal cap to be mounted onto the connector of FIG. 10.
FIG. 15 is a view showing a further embodiment of the medical instrument of the present invention.

One of the projecting slip stoppers 43a is connected with a flexible strap 45 having a seal cap 46 at its end part. At the center of the interior of the seal cap 46, an inner cylindrical part 46b protrudes, and a plurality of slip stopping grooves 46a are circumferentially formed in the outer surfaces. The inner cylindrical part 46b has an outer diameter sufficient to seal on a liquid flowing path 47 of the second connecting part 41. The path 47 is formed by communication between the first and second connecting parts 40 and 41.

Thread ridges 44 are formed on the both sides of the outer circumference at the front end of the second connecting part 41. The interior of the seal cap 46 cooperates with said thread ridges 44 under pressure. The second connecting part 41 is formed with a large diameter opening 48a at the rear end of the interior as shown in FIG. 13 into which said second medical liquid introducing tube 15 is inserted.

FIG. 15 is an outlined view showing a high calorie liquid transferring bag set 51 with the attached above mentioned connector 50. A structure and manner of use of the bag set, omitting the connector 50, is the same as the bag set 11 shown in FIG. 3.

The medical liquid is introduced from the bottle 36 into the bag body 12. After having accomplished a predetermined preparation thereof, the first connecting part 40 and the second connecting part 41 of the connector 50 are twisted by the fingers in opposition to each other (may be pressed and bent) so as to break the breaking portion 42. Thus, the first and second parts 40 and 41 are separated, and the seal cap 46 is crowned onto the opening of the second connecting part 41. If the seal cap 46 is urged by rotating it, the inner cylindrical part 46b is guided by the thread ridge 44 contacting to the inside of the seal cap 46 and is urged into the opening (the liquid flowing path 47) of the second connecting part 41. The seal cap 46 is never lost because it is connected to the strap 45.

As the medical liquid, there can be used amino acid, glucose, Ringer's solution, physiological salt solution, etc. other than high calorie medical liquid. The inventive connector can be disposed on the half way of a connecting tube between a parent bag and a child bag, and after the separated constituent parts of the blood in the parent bag have ben moved to the child bag via the connecting tube, the first connecting part and the second connecting part are divided to break the connecting tube. The connector is preferably suited to such medical instruments which require division of the tube sending the medical liquids and humors under a germless condition.

According to the present invention, the connector attached to the bendable tube is broken at the breaking portion and the opening created thereby is provided with the seal cap, to thereby easily separate the bendable tube with securing the air sealing and the liquid sealing.

It will be understood that each of the elements described above, or two or more together, may also find a useful application in other types of constructions differing from the types described above.

While the invention has been illustrated and described as embodied in a medical connector for attaching to liquid introducing tube, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A medical connector connected to a medical bag for separating the liquid introducing tube substantially half way thereof, the medical connector comprising a first connecting part connectable with a liquid introducing tube at a separating side; a second connecting part connectable to the liquid introducing tube at a back side and being integral with said first connecting part; a breaking notched portion which is breakable at finger pressure; slip preventing projections provided on an outer circumference of said connecting parts; and sealing means for sealing an opening of said second connector part after breaking said breaking portion, said sealing means including a seal cap which is attached to said second connecting part by a strap and having a sealing portion for water-tightly sealing the opening of said second connecting part.

2. A medical connector connected to a medical bag for separating the liquid introducing tube substantially half way thereof, the medical connector comprising a first connecting part connectable with a liquid introducing tube at a separating side; a second connecting part connectable to the liquid introducing tube at a back side and being integral with said first connecting part; a breaking notched portion which is breakable at finger pressure; and sealing means for sealing an opening of said second connector part after breaking said breaking portion, said sealing means including a seal cap which is attached to said second connecting part by a strap and having a sealing portion for water-tightly sealing the opening of said second connecting part, said second connecting part having screw shaped projections for pressing an inner portion of said sealing cap on an outer portion of said second connecting part.

3. A medical connector as defined in claim 2, wherein said seal cap has a female screw on said inner portion.

4. A medical connector as defined in claim 2, wherein said sealing portion of said seal cap has a cylindrical body for water-tightly sealing the opening of said second connecting part.

5. A medical connector as defined in claim 2, wherein said connecting parts are provided with slip preventing projections on an outer circumference, said slip preventing projections of said second connecting part being greater than the slip preventing projections of said first connecting part.

6. A medical connector as defined in claim 1, wherein said slip preventing projections of said second connecting part are formed with a support rib.

7. A medical instrument, comprising a liquid transferring bag; a liquid introducing tube connected with said bag and having two tube portions; a branching tube connected at a front end of said liquid introducing tube to be connected to said liquid transferring bag; a liquid introducing needle connected to said branching tube; a medical connector attached to said liquid introducing tube and including a first connecting part connectable with a liquid introducing tube at a separating side, a second connecting part connectable to the liquid introducing tube at a back side and being integral with said first connecting part, a breaking notched portion which is breakable at finger pressure, slip preventing projections provided on an outer circumference of said connecting parts and sealing means for sealing an opening of said second connector part after breaking said breaking portion, said sealing means including a seal cap which is attached to said second connecting part by a strap and having a sealing portion for water-tightly sealing the opening of said second connecting part; and a tube clamp provided at least at one side of said liquid introducing tube and connected to said first and second connecting parts of said connector.

* * * * *